(12) United States Patent
Grundler et al.

(10) Patent No.: US 7,604,480 B2
(45) Date of Patent: Oct. 20, 2009

(54) REDUCTION OF THE SHRINKAGE FORCE OF TOOTH FILLINGS

(75) Inventors: Andreas Grundler, Wuppertal (DE); Marcus Hoffmann, Usingen (DE)

(73) Assignee: Heraeus Kulzer GmbH, Hanau (DE)

( * ) Notice: Subject to any disclaimer, the term of this patent is extended or adjusted under 35 U.S.C. 154(b) by 184 days.

(21) Appl. No.: 11/557,260

(22) Filed: Nov. 7, 2006

(65) Prior Publication Data

US 2007/0142496 A1   Jun. 21, 2007

(30) Foreign Application Priority Data

Nov. 9, 2005   (DE) .................. 10 2005 053 775

(51) Int. Cl.
*A61C 5/00* (2006.01)
*A61K 6/02* (2006.01)

(52) U.S. Cl. .................. 433/217.1; 433/228.1; 523/118

(58) Field of Classification Search .................. 523/118; 433/217.1

See application file for complete search history.

(56) References Cited

U.S. PATENT DOCUMENTS

| 3,709,866 | A | * | 1/1973 | Waller ..................... 522/96 |
|---|---|---|---|---|
| 4,886,843 | A | | 12/1989 | Walton |
| 5,750,590 | A | | 5/1998 | Schaefer et al. |
| 6,063,831 | A | | 5/2000 | Kubo et al. |
| 6,709,271 | B2 | | 3/2004 | Yin et al. |
| 6,783,810 | B2 | | 8/2004 | Jin et al. |
| 6,855,197 | B2 | | 2/2005 | Su et al. |
| 2003/0175659 | A1 | | 9/2003 | Tiba et al. |
| 2003/0175660 | A1 | | 9/2003 | Yin et al. |
| 2005/0065227 | A1 | | 3/2005 | Condon |

FOREIGN PATENT DOCUMENTS

| DE | 198 51 038 | 7/1999 |
|---|---|---|
| DE | 199 13 890 | 9/2000 |
| DE | 10 2004 031 524 | 1/2006 |
| EP | 1 393 705 | 6/1989 |
| EP | 0 329 268 | 8/1989 |
| EP | 0329268 | 8/1989 |
| EP | 0 684 034 B1 | 3/2000 |
| EP | 1 393 705 | 3/2004 |

OTHER PUBLICATIONS

Marcelo Giannini, et al., Influence of Activation Mode of Dual-Cured Resin Composite Cores and Low-Viscosity Composite Liners on Bond Strength to Dentin Treated With Self-Etching Adhesives, The Journal of Adhesive Dentistry, XP008092165, 2004, pp. 301-306.

* cited by examiner

*Primary Examiner*—Tae H Yoon
(74) *Attorney, Agent, or Firm*—Norris McLaughlin & Marcus P.A.

(57) ABSTRACT

A self-curing or dual-curing, low viscosity composite is used for the fabrication of a dental liner capable of polymerization in 2 stages with 2 curing times and delayed polymerization characteristics that is designed for use at the cavity wall in the form of a thin layer.

2 Claims, No Drawings

REDUCTION OF THE SHRINKAGE FORCE OF TOOTH FILLINGS

The invention relates to the reduction of the shrinkage force of tooth fillings.

Acrylate/methacrylate-based light-curing materials experience volume shrinkage during radical polymerization because the distance between molecules is reduced and the density is increased during the polymerization. The shrinkage can be reduced markedly by adding inorganic fillers, such as e.g. dental glasses or pyrogenic silicic acids, since this results in a reduced monomer fraction per volume unit and the fillers do not shrink during polymerization.

Shrinkage of the volume is of great clinical significance in dental applications since the material shrinkage transmits tensile forces to the cavity wall. If a maximal force is exceeded, this shrinkage force, in an extreme case, can lead to detachment from the cavity wall. Bacteria and/or their acidic metabolic products can then penetrate into the marginal gap thus produced and secondary caries may manifest subsequently.

Looking at the time profile of the shrinkage force, the following typical finding is evident: Right after polymerization, volume shrinkage results in an initial value of the shrinkage force which then increases due to post-polymerization over approx. 24 h to reach a maximal value.

Subsequently, water uptake (due to storage in water at the laboratory and/or from the saliva in the mouth) leads to a low-level expansion of the volume of the composite after a few days to weeks; this allows the tension forces to relax again and returns them to a lower level.

As a result, the crucial parameter is the max. shrinkage tension value after approx. 24 h, since it represents the maximal force acting on the composite system made up of composite/adhesive/tooth.

There has been no paucity of attempts to provide low shrinkage dental materials: DE 199 05 093 A1 recommends the use via ring-opening metathesis polymerization (ROMP) of curing bicyclic monomers. According to DE 198 51 038 A1, the addition of acryloylmorpholine, coumarone resin, vinylstearate, polyvinylacetate or alcohol tensides prior to polymerization is effective in fighting shrinkage. According to U.S. Pat. No. 5,750,590, cationic-polymerizable "oxetanes" (trimethyleneoxides) show only little shrinkage and are therefore also suitable for use as dental materials with reduced shrinkage. U.S. Pat. No. 6,855,197 B2 describes epoxide resin-based reduced-shrinkage filling materials containing nano-scale inorganic oxides as fillers. According to U.S. Pat. No. 6,709,271 B2, the use of a filler mixture made up of spherical-shaped filler of a particle size of 200-500 nm and submicron-sized filler of a particle size of 20-80 nm leads to shrinkage of up to 1.8% after polymerization.

The subject matter of the present application relates mainly to the shrinkage force and the reduction thereof: Aside from the material properties discussed above in an exemplary fashion, the shrinkage force is also affected by processing parameters:

Light Power

A light-curing device with pulsed operation for remedying shrinkage force problems has been proposed in DE 199 13 890 A1.

Polymerization Kinetics

Lower shrinkage forces can be attained for identical composite materials by slower polymerization at lower light power initially and only later increasing the light power to the maximal value (soft start polymerization). The lower light power at the start causes the composite material to remain flowable for longer and thus can compensate for and reduce tensions better (J. Esthet. Restor. Dent. (2003) 15, 93-104). US 20050065227 A1 suggests that the early stages of shrinkage in the use of multifunctional photoinitiators occur while the material is still elastic. This is said to ultimately lead to lower shrinkage tensions.

Geometry of the Restoration

Shrinkage forces can be minimized through the use of an incremental technique in the build-up of the restoration (U.S. Pat. No. 6,783,810 B2). However, the more layers need to be cured individually, the more time the attending dentist needs to perform this work.

It is the object of the present invention to compensate, at least in part, for the shrinkage force caused by the curing of the filling composite.

This object is met by a self-curing or dual-curing (simultaneously self- and light-curing) low viscosity composite is provided for application as liner (hereinafter referred to as liner) that is designed for use at the cavity wall in the form of a thin layer and that has delayed polymerization characteristics.

This new liner is provided with a very low level of light-activated initiators and/or a low level of a redox-initiator system. The novel self-curing liner has a curing time of a few, e.g. 2 to 10, minutes, in which a first strength is attained. The subsequent complete polymerization proceeds over several, e.g. 1 to 3, hours. The novel dual-curing liner ideally has only a small curing depth of <1 mm upon light activation and thus undergoes only superficial gelation initially due to the action of light[1]. The subsequent complete polymerization proceeds in self-curing mode and also takes several hours.

[1] The curing depth can be set by adding components, e.g. fillers or pigments, that are impervious to light.

Accordingly, the novel dual-curing, low viscosity liner is initially subject to light-curing with some gelation and simultaneous and/or subsequent complete self-curing.

In practical application, the tooth to be treated is initially etched and bonded according to the total etch technique or treated with a self-etching adhesive before a thin layer of the novel liner is applied to the cavity wall.

Referring to the novel dual-curing liner, the surface structure is subsequently fixed by the action of light and then the cavity remaining in the novel liner is filled with a classical filling composite which is then also cured by the action of light in the final step.

Due to the polymerization of the novel liner being delayed and proceeding slowly, the liner cures in a delayed fashion, can thus flow for a longer period of time and compensate, at least in part, for the shrinkage and/or shrinkage force of the filling composite that is ultimately used.

The novel liner preferably comprises the following components:

Monomer component: from 10 wt-% to 40 wt-%,
Cross-linker component: from 10 wt-% to 40 wt-%,
Filler component: from 20 wt-% to 80 wt-%,
Photoinitiator: up to 0.5 wt-%,
Initiator system: from 0.1 wt-% to 1.2 wt-%.

The monomers used commonly in dentistry can be used as monomers: examples are monofunctional monomers for radical polymerization such as mono(meth)acrylates, methyl-, ethyl-, butyl-, benzyl-, furfuryl- or phenyl(meth)acrylate, polyfunctional monomers such as polyfunctional acrylates and/or methacrylates, e.g. bisphenol-A-di(meth)acrylate, bis-GMA (an addition product of methacrylic acid and bisphenol-A-diglycidylether), UDMA ("urethanedimethacrylate", e.g. an addition product of 2-hydroxyethylmethacrylate and 2,2,4-hexamethylenediisocyanate), di-, tri- or tetraethyleneglycoldi(meth)acrylate, decandioldi(meth)acrylate, dodecandioldi(meth)acrylate, hexyldecandioldi(meth)acrylate, trimethylolpropantri(meth)acrylate, pentaerythritoltetra(meth)acrylate and butandioldi(meth)acrylate.

Bis-GMA, TEDMA (triethyleneglycoldimethacrylate), UDMA (urethanedimethacrylate), TCD-di-HEMA (bis(methacryloyloxymethyl)tricyclo[5.2.1.0$^{2,6}$]decane) and TCD-di-HEA (bis-(acryloyloxymethyl)tricyclo[5.2.1.0$^{2,6}$]decane) are preferred.

Cross-linker: Cross-linker monomers are e.g. 2,2-bis-4-(3-methacryloxy-2-hydroxypropyl)-phenyl-propane) (Bis-GMA), i.e. the product of the conversion of glycidylmethacrylate and bisphenol-A (OH group-containing), and 7,7,9-trimethyl-4,13-dioxo-3,14-dioxa-5,12-diazahexadecan-1,16-diyl-dimethacrylate (UDMA), i.e. the urethanedimethacrylate made from 2 mol 2-hydroxyethylmethacrylate (HEMA) and 1 mol 2-2,4-trimethylhexamethylenediisocyanate (urethane group-containing). Moreover, products of the conversion of glycidylmethacrylate and other bisphenols, such as e.g. bisphenol-B (2,2'-bis-(4-hydroxyphenyl)-butane), bisphenol-F (2,2'-methylenediphenol) or 4,4'-dihydroxydiphenyl, as well as products of the conversion of 2 mol HEMA or 2-hydroxypropyl(meth)acrylate and, in particular 1 mol, of known diisocyanates, such as e.g. hexamethylenediisocyanate, m-xylylenediisocyanate or toluylenediisocyanate are suitable as cross-linker monomers.

Aside from the oxides, TiO$_2$, ZrO$_2$, Al$_2$O$_3$, SiO$_2$, other metal oxides such as tin oxide, metal sulfates, other oxides of the subgroups of the periodic system, fluoride-releasing substances, pyrogenic or precipitant silicic acids, dental glasses such as aluminosilicate glasses or fluoroaluminosilicate glasses, strontium silicate, strontium borosilicate, lithium silicate, lithiumaluminumsilicate, phyllosilicates, zeolithes, amorphous spherical fillers based on oxides or mixed oxides (SiO$_2$, ZrO$_2$ and/or TiO$_2$), metal oxides with primary particle sizes of approx. 40 to 300 nm, splinter polymers with particle sizes of 10-100 µm (refer to R. Janda, Kunststoffverbundsysteme, VCH Verlagsgesellschaft, Weinheim, Germany, 1990, pages 225 ff.) or mixtures thereof can be used as fillers. Moreover, reinforcing agents such as glass fibers, polyamide or plastic fibers can be incorporated.

Usually, the filler content preferably is 5 to 80 wt-%, particularly 20 to 80 wt-%, relative to the total mass of the dental material.

Moreover, the dental materials according to the invention can also contain common substances for dental materials, e.g. from the groups of pigments, stabilizers, antimicrobial additives, UV absorbers, thixotropic agents, catalysts.

Rather low amount of those additives are used, in total 0.01 to 3.0, in particular 0.01 to 1.0 wt-% relative to the total mass of the dental material.

Depending on the type of polymerization initiator used, the compositions can be cured by means of thermal, photochemical or redox-induced radical polymerization.

Preferred examples of thermal initiators are the known peroxides such as e.g. dibenzoylperoxide, dilaurylperoxide, tert.-butylperoctoate or tert.-butylperbenzoate as well as azobisisobutyroethylester, azobisisobutyronitrile, azobis-(2-methylpropionamidine)dihydrochloride, benzopinacol or 2,2-dimethylbenzopinacol.

Preferred photoinitiators are benzophenone, benzoin as well as the derivatives thereof or alpha-diketones or the derivatives thereof such as 9,10-phenanthrenequinone, diacetyl or 4,4-dichlorobenzil. It is particularly preferred to use camphor quinone and 2,2-dimethoxy-2-phenyl-acetophenone and, particularly preferred, alpha-diketones in combination with amines as reduction agents, such as e.g. 4-(N,N-dimethylamino)-benzoic acid ester, N,N-dimethylamino-ethylmethacrylate, N,N-dimethyl-sym.-xylidine or triethanolamine. Moreover, acylphosphines, such as e.g. 2,4,6-trimethylbenzoyldiphenyl- or bis(2,6-dichlorebenzoyl)-4-N-propylphenyl-phosphineoxide are particularly well suited.

It is preferred to use redox initiator combinations, such as e.g. combinations of benzoyl- or laurylperoxide and N,N-dimethyl-sym.-xylidine or N,N-dimethyl-p-toluidine as initiators for the polymerization that is carried out at room temperature.

Suitable fillers and pigments are known to the expert and can be, for example, Al$_2$O$_3$, MgO, ZrO$_2$, TiO$_2$, Y$_2$O$_3$, YF$_3$, Fe$_2$O$_3$, SiO$_2$, gold or silver particles with TiO$_2$ being preferred.

The composition of two liners according to the invention is described in the following examples for the purposes of illustration:

EXAMPLE 1

Liner provided in the form of two pastes to be cured by means of photopolymerization and redox polymerization:

|  | wt % |
|---|---|
| Paste A | |
| Bis-GMA | 35.41% |
| Triethyleneglycoldimethacrylate | 23.61% |
| silan. Aerosil | 37.44% |
| Titanium dioxide | 3.12% |
| N,N-bis-(2-hydroxyethyl)-p-toluidine | 0.41% |
| DL-camphorquinone | 0.01% |
| Paste B | |
| Urethanedimethacrylate | 37.29% |
| Triethyleneglycoldimethacrylate | 16.13% |
| silan. Aerosil | 42.56% |
| Titanium dioxide | 3.12% |
| BPO (paste 50%) | 0.84% |
| BHT | 0.06% |

EXAMPLE 2

Liner provided in the form of two pastes to be cured by means of redox polymerization:

|  | wt % |
|---|---|
| Paste A | |
| Bis-GMA | 35.41% |
| Triethyleneglycoldimethacrylate | 23.61% |
| silan. Aerosil | 40.57% |
| N,N-bis-(2-hydroxyethyl)-p-toluidine | 0.41% |
| Paste B | |
| Urethanedimethacrylate | 37.29% |
| Triethyleneglycoldimethacrylate | 16.13% |
| silan. Aerosil | 45.68% |
| BPO paste | 0.84% |
| BHT | 0.06% |

The invention claimed is:

1. A method for compensating for the shrinkage forces produced by a dental filling during polymerization, which comprises applying a liner to the walls of a cavity to be filled by said dental filling, prior to placing said dental filling in said cavity, said liner being formed of a dual-curing, low viscosity composite containing polymerizable monomer(s), crosslinker, initiator and light-impervious components selected from the group consisting of fillers and pigments, and being capable of polymerization in two stages, said two stages being a first stage, in which the surface of said liner is cured, to a depth of <1 mm by light curing with gelation, and a simultaneous and/or subsequent second stage, in which the remainder of said liner is completely cured by thermal or redox-induced self-curing, the first stage having a curing time of 2 to 10 minutes and the second stage having a curing time of 1 to 3 hours.

2. Method according to claim 1, wherein the composite comprises the following components:
Monomer component: from 10 wt-% to 40 wt-%
Cross-linker component: from 10 wt-% to 40 wt-%
Filler component: from 20 wt-% to 80 wt-%
Photoinitiator: 0.01 wt. % to 0.5 wt-%
Thermal or redox initiator system: from 0.1 wt % to 1.2 wt %.

* * * * *